(12) United States Patent
Gallem et al.

(10) Patent No.: US 9,095,676 B2
(45) Date of Patent: *Aug. 4, 2015

(54) NEBULISER FOR VENTILATION MACHINES AND A VENTILATION MACHINE COMPRISING SUCH A NEBULISER

(71) Applicant: PARI Pharma GmbH, Starnberg (DE)

(72) Inventors: Thomas Gallem, Münich (DE); Uwe Hetzer, Münich (DE)

(73) Assignee: PARI Pharma GmbH, Starnberg (DE)

( * ) Notice: Subject to any disclaimer, the term of this patent is extended or adjusted under 35 U.S.C. 154(b) by 120 days.

This patent is subject to a terminal disclaimer.

(21) Appl. No.: 13/783,642

(22) Filed: Mar. 4, 2013

(65) Prior Publication Data

US 2013/0174840 A1    Jul. 11, 2013

Related U.S. Application Data

(63) Continuation of application No. 12/990,994, filed as application No. PCT/EP2009/055469 on May 6, 2009, now Pat. No. 8,720,435.

(30) Foreign Application Priority Data

May 9, 2008    (DE) .......................... 10 2008 022 987

(51) Int. Cl.
*A61M 11/00*    (2006.01)
*A61M 15/00*    (2006.01)
(Continued)

(52) U.S. Cl.
CPC .............. *A61M 16/14* (2013.01); *A61M 11/005* (2013.01); *A61M 15/0036* (2014.02);
(Continued)

(58) Field of Classification Search
CPC ............ A61M 11/005; A61M 15/001; A61M 15/0085; A61M 16/142
USPC ............. 128/202.27, 203.12, 203.15, 200.14, 128/200.16, 200.18, 200.23
See application file for complete search history.

(56) References Cited

U.S. PATENT DOCUMENTS 5,474,058 A    12/1995    Lix
5,518,179 A     5/1996    Humberstone et al.
(Continued)

FOREIGN PATENT DOCUMENTS

DE    101 06 010 C1      7/2002
DE    10 2005 038619 A1  2/2007
(Continued)

OTHER PUBLICATIONS

Examination Report dated Apr. 4, 2013 from corresponding Australian Patent Application No. 2009245802.
(Continued)

*Primary Examiner* — Kristen Matter
(74) *Attorney, Agent, or Firm* — Wolf, Greenfield & Sacks, P.C.

(57) ABSTRACT

Atomizer for a ventilation machine with a ventilator, including a body with a first connection for connecting the atomizer to a ventilator and a second connection for connecting the atomizer to a line leading to a patient, wherein the body forms a flow channel from the first connection to the second connection; and an atomizing device for atomizing a fluid; wherein the atomizing device is disposed between the first connection and the second connection in the flow channel and adapted so that the fluid can be atomized substantially parallel to, and preferably in, the flow direction from the first connection to the second connection.

16 Claims, 7 Drawing Sheets

(51) Int. Cl.
*A61M 16/00* (2006.01)
*B05B 17/06* (2006.01)
*A61M 16/14* (2006.01)
*A61M 16/08* (2006.01)
*A61M 16/04* (2006.01)
A61M 16/18 (2006.01)
A61M 16/20 (2006.01)

(52) U.S. Cl.
CPC ...... *A61M 16/0057* (2013.01); *A61M 16/0465* (2013.01); *A61M 16/0816* (2013.01); *A61M 16/0833* (2014.02); *A61M 15/00* (2013.01); *A61M 15/001* (2014.02); *A61M 16/183* (2013.01); *A61M 16/208* (2013.01); *A61M 2016/0021* (2013.01)

(56) References Cited

U.S. PATENT DOCUMENTS

| | | | |
|---|---|---|---|
| 5,666,946 | A | 9/1997 | Langenback |
| 6,851,626 | B2 | 2/2005 | Patel et al. |
| 7,971,588 | B2 | 7/2011 | Fink et al. |
| 8,375,947 | B2 | 2/2013 | Alston et al. |
| 8,720,435 | B2 * | 5/2014 | Gallem et al. ........... 128/200.16 |
| 2003/0072717 | A1 | 4/2003 | Reinhold et al. |
| 2003/0196660 | A1 | 10/2003 | Haveri |
| 2005/0150505 | A1 | 7/2005 | Burrow et al. |
| 2006/0289002 | A1 | 12/2006 | Hetzer et al. |
| 2007/0101994 | A1 | 5/2007 | Waters |
| 2008/0000470 | A1 | 1/2008 | Minocchieri et al. |
| 2008/0299049 | A1 | 12/2008 | Stangl |
| 2009/0293868 | A1 | 12/2009 | Hetzer et al. |

FOREIGN PATENT DOCUMENTS

| | | |
|---|---|---|
| EP | 0 945 151 B1 | 9/1999 |
| EP | 1 818 070 A2 | 8/2007 |
| WO | WO 2005/048982 A2 | 6/2005 |
| WO | WO 2007/020073 A1 | 2/2007 |

OTHER PUBLICATIONS

English translation of the International Preliminary Report on Patentability mailed Feb. 24, 2011 from International Application No. PCT/EP2009/055469.

European Search Report mailed Jan. 26, 2015 from corresponding European Patent Application No. 14188616.8.

* cited by examiner

NEBULISER FOR VENTILATION MACHINES AND A VENTILATION MACHINE COMPRISING SUCH A NEBULISER

CROSS REFERENCE TO RELATED APPLICATIONS

This application is a continuation of U.S. application Ser. No. 12/990,994 filed Feb. 1, 2011, which is a 371 of PCT/EP2009/055469 filed May 6, 2009, now U.S. Pat. No. 8,720,435, which claims the priority benefit of German Appln. No. 10 2008 022 987.3 filed May 9, 2008, which are hereby incorporated by reference to the maximum extent allowable by law.

FIELD OF THE INVENTION

The present invention relates to nebulisers for ventilation machines and in particular to nebulisers for introducing an active ingredient in aerosol form into the respiratory air that is supplied to a patient for assisted or substitute ventilation. A nebuliser is hereby to be understood as any device for generating an aerosol. A ventilation machine is to be understood as a ventilation device that supplies patients intubated or tracheotomised using an endotracheal tube with a flaw of air of up to 120 l/min, preferably between 1 and 50 l/min, at a pressure of between 0 and 100 mbar and preferably between 3 and 45 mbar.

The present invention furthermore also relates to a ventilation machine comprising such a nebuliser.

BACKGROUND

Nebulisers for ventilation machines are well known in the prior art. For example, WO 2005/048982 A2 discloses such a nebuliser. This nebuliser comprises a body having a first connection that comprises two connecting pieces for connecting the nebuliser to an air supply line and an air exhaust line of the ventilation device. Opposite the first connection, the body comprises a second connection that again has two connecting pieces which are to be connected via a Y-piece and two tubes with a line leading to the patient. Two separate flow channels that are connected via a connecting channel are formed in the body, one (first one) of which serves the flow of respiratory air from the air supply line to the patient and the other (second one) of which serves the flow of consumed air from the patient into the air exhaust line. A non-return valve that allows a flow solely in the direction of the patient is disposed in the first flow channel upstream of a connection of a nebulising device to the first flow channel. Furthermore, the nebulising device is coupled perpendicular, similar to a T connection, to the first flow channel, with the aerosol being supplied in a direction perpendicular to the direction of flow in this first flow channel.

The problem with this design is on the one hand that owing to the non-return valve, an element is integrated in the air supply line, i.e. in the line that leads to the patient, which could have serious consequences should it malfunction.

There is on the other hand the problem that the aerosol is introduced into the flow perpendicular to the direction of flow of the respiratory air through the body, and thus a high deposition of the aerosol on the surfaces of the flow channel occurs, which has a high loss associated therewith.

It is known from other fields of technology to prevent deposition of the aerosol on surfaces in particular of the nebulisation chamber in that the nebulising device nebulises in a direction that is parallel to a flow towards the patient.

US-A-2003/0072717, for example, discloses an inhalation device wherein a nebulising device is arranged in a closed and bypassed housing. The housing is disposed in a flow channel of the inhalator, which comprises a mouthpiece. The nebulising device thereby nebulises in the direction of the mouthpiece. However, dead volumes, flow resistance by the nebulising device as well as the filling thereof only play minor roles therein. In ventilation machines, however, the nebulisers must meet predefined criteria in this regard. EP-A-1 818 070 also discloses an inhalation therapy device having such a nebulisation direction, in this case, however, for premature babies. The system (requires the patient to be able to breathe on their own and) is specifically adapted to the small line cross-sections with an inner diameter of between 2 mm and 3.5 mm for premature babies such that air may easily pass around the nebulisation device without flow resistance occurring. Furthermore, since the patient is able to breathe on their own, the system operates at a low pressure of up to 15 mbar. Moreover, filling of the nebuliser with a fluid to be nebulised is not necessary or intended when the system is in operation since operation can be interrupted for filling and/or a loss in pressure in the system can be accepted without risk. Therefore, the above-described and comparable systems from the prior art were not transferable for use in ventilation machines.

SUMMARY

The object of the present invention is therefore to create a nebuliser for ventilation machines, wherein the deposition of aerosol on the surfaces of the flow channel and the losses associated therewith are reduced and failures of vulnerable elements can be avoided. The mode of operation of the ventilation machine must at the same time not be impaired by the nebuliser, i.e. no flow resistance may be generated, the nebuliser must be airtight at a certain positive pressure (for example 100 mbar), filling of the nebuliser with the fluid to be nebulised must also be possible during operation of the ventilation device without a loss in pressure in the system, and a dead space in the nebuliser must not take up too much volume, etc.

This object is solved by a nebuliser having the features of patent claim 1. Advantageous further developments of the present invention are mentioned in the sub-claims.

The idea forming the basis for the present invention is to reposition the nebulising device in the flow channel such that the aerosol generation occurs by nebulising the fluid parallel to the direction of flow in the flow channel, instead of coupling the nebulising device perpendicular to the direction of flow by means of a T-piece-like arrangement, such as is the case in the prior art.

The present invention accordingly proposes a nebuliser for ventilation machines, which comprises a body having a first connection for connecting (for example indirectly via a tube) the nebuliser to a ventilation device and a second connection for connecting (for example indirectly via a tube) the nebuliser to a line leading to the patient, said body forming a flow channel, and in particular only one flow channel, from the first connection to the second connection. That is to say, in a specific embodiment, the body forms only one flow channel, through which respiratory air flows from the first connection to the second connection during inhalation and consumed air flows from the second connection to the first connection during exhalation. The line that leads to the patient can be composed of the so-called catheter mount (double swivel connector) and the endotracheal tube as well as optionally of other elements. In a specific embodiment, the connection to the ventilation device can be effected by way of both the air supply line for supplying respiratory air as well as the air exhaust line for expelling consumed air such that the nebuliser simultaneously forms a Y-piece. However, it goes without saying that the first connection of the body may also be connected only to the air supply line, such that a possible Y-piece is arranged only downstream of the second connection. The nebuliser of the present invention furthermore comprises a nebulising device for nebulising a fluid. The fluid is preferably a liquid composition that preferably contains at least one active ingredient (see below). A nebulising device is to be understood as any aerosol generator or producer by means of which the fluid can be transformed into an aerosol form. According to the invention, the nebuliser is characterised in that the nebulising device is disposed in the flow channel between the first connection and the second connection, and is configured such that the fluid can be nebulised substantially parallel to, and preferably in, the direction of flow from the first connection to the second connection. In other words, respiratory air passes around the nebulising device in the inhalation cycle and the fluid to be nebulised is nebulised parallel to, and preferably in, the direction of the respiratory air flow such that an aerosol flow is generated parallel to, preferably in, the direction of flow of the first respiratory air, as a result of which the impaction and thus deposition on surfaces in the flow channel is reduced and the aerosol can be supplied to the line system and transported to the patient with the smallest amount of loss possible. The wording "substantially" is to be understood in this respect such that the aerosol flow may also have a deviation of up to 45° to the direction of flow of the respiratory air.

So as to regulate the respiratory air, ventilation devices produce a continuous basic flow (a so-called "bias flow"). Outside of an inhalation cycle, wherein respiratory air is transported to the patient via the air supply line, this bias flow, which may be in the magnitude of up to 30 l/min, normally flows directly into the air exhaust line from the air supply line. To achieve this without the bias flow passing the nebulising device and nebulised fluid thus permanently flowing into the air exhaust line, which would lead to a significant inefficiency of the system, the nebuliser of the present invention preferably comprises a first connection that is designed to connect with an air supply line coming from the ventilation device and an air exhaust line leading to the ventilation device in such a manner that a side-flow channel (bypass) from the air supply line to the air exhaust line is formed on the side of the nebulising device that is opposite the second connection.

The air supply line and the air exhaust line can thereby be formed by a common tube that is divided into two sections. This division may be formed either by a partition in the tube or by a coaxial tube, i.e. two tubes arranged one inside the other. The common tube is to be connected to the first connection of the nebuliser. The first connection and the common tube are thereby configured in such a manner that a bypass is formed between the nebulising device and the front face of the partition and/or of the inner tube of the coaxial tube, which is facing the nebulising device. The bypass allows the bias flow to flow, outside of an inhalation cycle, directly into the air exhaust line from the air supply line without flushing any possibly nebulised fluid into the air exhaust line. The efficiency of the system can be significantly improved as a result.

It is, of course, alternatively also conceivable for the air supply line and the air exhaust line to each be formed by a separate tube. In this design, it is preferred for the first connection to have a first connecting piece for connection to the air supply line and a second connecting piece for connection to the air exhaust line, each of which may be formed by a tube. The bypass is then formed in the body itself between the first connecting piece and the second connecting piece and, outside of an inhalation cycle, allows a flow from the air supply line into the air exhaust line. This design furthermore leads to a tilt-stable unit of the nebuliser being formed by the two connecting pieces and the opposite second connection.

As already mentioned at the start, the nebuliser must also allow filling of a fluid container during ventilation without a loss of pressure in the system. Therefore a vibrating membrane (oscillating membrane) is Preferably used as the nebulising device, the membrane being provided with a plurality of openings (micro openings) for nebulising the fluid. The membrane is preferably arranged perpendicular to the direction of flow from the first connection to the second connection so as to achieve nebulisation in the direction of flow or parallel to the direction of flow. The wording "substantially" is to be understood in this respect such that the membrane may also be arranged in the flow channel at a slight gradient deviating by up to 45° from the perpendicular. From the point of view of flow technology, the membrane is thereby preferably designed so as to be circular, however it may also be oval. Owing to this design of the aerosol generator (nebulising device) with a membrane comprising very small openings, through which a flow out of the flow channel and out of the system is not possible, it is ensured in a simple manner that a loss in pressure via the nebulising device is prevented, even when the fluid container is opened, for example the lid of the fluid container is unscrewed for filling.

Furthermore, a fluid container for receiving the fluid to be nebulised, which is connected to the body, is provided, as is a nebulisation chamber into which the fluid is to be nebulised, with the membrane being arranged between the fluid container and the nebulisation chamber. The fluid container is connected to the body in such a manner that it can be coupled and uncoupled. Instead of directly accommodating the fluid, the fluid container may also have a fluid communication interface and be configured to receive a fluid-containing ampoule that comes into fluid connection with the fluid container via the fluid communication interface. The fluid communication interface may, for example, be formed by an opening device (a hollow spike) and may be configured to receive a fluid-containing ampoule to be opened by the opening device, similar to that described, for example, in WO 2007/020073 for a conventional nebuliser/aerosol generator, to which reference is made for further details. It is also conceivable for the fluid container to have a hollow needle and for a valve to be provided in the ampoule, which is opened by the needle when the ampoule is received by the fluid container.

In order to further minimise deposition and thus loss at the surfaces of the flow channel, it is, as mentioned, particularly preferred to nebulise the fluid in the inhalation cycle in the direction of flow of the respiratory air, for which purpose the nebulisation chamber is preferably disposed between the membrane and the second connection that is to be connected to the line leading to the patient.

It is furthermore necessary for the fluid container to supply a constant dosage to the nebuliser membrane up to a gradient of 45° in every direction about the direction of flow from the first to the second connection so that a reliable and uniform nebulisation or aerosol generation can take place. For this purpose, the unit consisting of the body and the fluid container can, as already mentioned, on the one hand be configured in a tilt-stable manner by the two connecting pieces and the opposite second connection. To further meet this requirement, it is, however, preferred for the fluid container to have a tapering in the direction of the membrane, which opens out into a fluid chamber that is closed by the membrane, with the tapering extending at least obliquely from a cylindrical portion of the fluid container to the fluid chamber.

It is particularly preferred for a partial section of the tapering that is facing away from the membrane to extend with an angle range of between 10° and 40° to the vertical and, in the case of a perpendicularly arranged membrane, preferably also to the membrane, i.e. a lower portion of the fluid container that is closed in cross-section is configured, for example, in the shape of a cone and the central axis of the cone has an angle range of between 10° and 30° to the vertical and, in the case of a perpendicularly arranged membrane, preferably also to the membrane.

As already mentioned at the start, the nebulising device, and in particular the membrane, is arranged in the flow channel such that air may flow around it. This flow-around portion of the flow channel is preferably configured in the radial direction between the membrane and the body in such a manner that a cross-sectional area of the flow-around portion substantially corresponds to the smallest cross-sectional area of a line of the ventilation device that leads to the patient, even though minor deviations are possible. The cross-sectional area of the flow portion is preferably larger than the smallest cross-section of a line, however is in any case at least almost the same. The cross-sectional area for adults is thereby in the range of approximately 400 mm². For small children, the cross-sectional area is in the range of approximately 80 to 180 mm². It is thereby prevented in the simplest manner that the flow resistance is increased too much owing to the integration of the nebuliser in the air supply and patient line and could lead to an impairment of the function of the ventilation device and/or the ventilation machine.

It is particularly preferred to hang the membrane in a frame surrounding the membrane by means of spokes, with the frame preferably also being circular or oval for reasons of flow technology, and preferably being configured with the same design as the membrane. Thus, a region though which a flow may pass is also formed between the frame and the membrane, and this region may form at least part of the flow-around portion of the flow channel. Further portions through which a flow may pass may optionally be provided between the frame and the body, and these portions may supplement the part of the flow-around portion provided between the membrane and the frame so as to achieve the desired cross-sectional area for the flow-around portion. Furthermore, the dead space resulting owing to the nebulisation chamber can be reduced by this design and the cross-section of the flow channel past the nebulising device can at the same time be increased without significantly increasing the external dimensions of the nebuliser.

In order to further increase the efficiency of the system, it may be preferred to control the nebuliser by way of a common or cooperating control with the ventilation device so that nebulisation of the fluid and thus aerosol generation can only be triggered during an inhalation cycle, i.e. nebulisation by the nebulising device only occurs when the patient inhales, be it assisted or forced by the ventilation device.

BRIEF DESCRIPTION OF THE DRAWINGS

Further advantages and features of the present invention, which can be combined alone or in combination with the above features, are apparent from the following description of preferred embodiments. This description is carried out with reference to the accompanying drawings, in which:

FIG. 1 shows a perspective view of a nebuliser according to a first embodiment, which is schematically coupled to a ventilation device;

FIG. 2 shows a top view of the nebuliser of FIG. 1;

FIG. 3 shows an upside down side view of the nebuliser in FIG. 1;

FIG. 4 shows a longitudinal section through the nebuliser of FIG. 1 along the line A-A in FIG. 2;

FIG. 5 shows a longitudinal section of the nebuliser of FIG. 1 along line B-B in FIG. 3;

FIGS. 6*a-f* show (a) a longitudinal section through the nebuliser of FIG. 1 along line A-A in FIG. 2 and (b) a longitudinal section of the nebuliser of FIG. 1 along line B-B in FIG. 3, both with a fluid flow during an inhalation cycle, and (c)-(d) show the same sections during an exhalation cycle, and (e)-(f) show the same sections between an exhalation cycle and an inhalation cycle;

FIG. 7 shows a longitudinal section though a nebuliser according to a second embodiment corresponding to the section in FIG. 4;

FIG. 8 schematically shows an alternative fluid container according to the invention; and FIG. 9 schematically shows a further alternative of a fluid container according to the invention.

DETAILED DESCRIPTION

In the different views, the same or corresponding elements are provided with identical reference numbers.

The nebuliser of the first embodiment as shown in FIGS. 1 to 5 is composed of three main components: a first body part 1, a second body part 2 and a nebulising device 3. The first and second body parts 1 and 2, which together form the body, are preferably made of plastic and are preferably produced in an injection moulding process.

The first body part 1 comprises a first connection 10, which is composed of two connecting pieces 11, 12. As is apparent from FIG. 1, the first connecting piece 11 is configured so as to connect with an air supply line of the ventilation device 100. The second connecting piece 12 is in turn coupled to an air exhaust line 102 of the ventilation device 100. The air supply line 101 and the air exhaust line 102 are thereby each formed by a separate tube (not shown), which may have, for example, an inner diameter of 22 mm for adults or an inner diameter of 10 mm and 15 mm for children. The connecting pieces 11, 12 are each configured such that it is possible to couple these conventional tubes to the connecting pieces. A bypass 13 is furthermore formed in the first body part 1, said bypass being arranged before (i.e. upstream in the direction of flow of the respiratory air) the nebulising device 3. This bypass ensures that a basic flow generated by the ventilation device 100 to regulate the respiratory air to a patient 104 can flow, outside of an inhalation cycle and/or an exhalation cycle of the patient 104, directly from the air supply line 101 into the air exhaust line 102 via the connecting piece 11, the bypass 13 and the connecting piece 12, without passing the nebulising device 3 (cf. FIGS. 6*e* and *f*). This basic flow has flow rate of up to 30 l/min. This basic flow is often also referred to as a "bias flow".

The first body part 1 furthermore also comprises a fluid container 14 for receiving a fluid to be nebulised. Possible fluids that are preferably in liquid form in the present embodiment are listed after the description of the preferred embodiments. The fluid container 14 is preferably an integral component of the first body part 1, however, it may also be configured such that it can be partially or completely coupled and uncoupled. It is also conceivable that the fluid container does not directly accommodate the fluid to be nebulised but rather that a device, for example a spike, is provided in the fluid container so as to open, for example pierce, an ampoule that can be inserted into the fluid container, out of which the fluid to be nebulised can be supplied to the nebulising device 3 and the later described fluid chamber 24.

According to the shown embodiment, the fluid container 14 has a substantially cylindrical portion 15 that has a substantially circular cross-section. An external screw thread 16 is formed on the outer circumferential surface of the cylindrical portion 15 at the end of the cylindrical portion 15 which is facing away from the nebulising device 3. An internal screw thread 17 of a lid 18, which is formed on the inner circumferential surface of the lid 18, can be engaged with this external screw thread 16 so that the lid 18 can be screwed onto the cylindrical portion 15 of the fluid container 14. The lid furthermore comprises a circumferential collar 19 on its inner surface, which, when the lid 18 is screwed on, sealingly engages, either directly or indirectly via a sealing material, with the inner surface of the cylindrical portion 14. Furthermore, the cylindrical portion 15 comprises a surrounding groove 20, in which one end of a lid securing means 21 (see FIG. 1) can be fixed, the other end of which can be attached to the mushroom-shaped projection 22 of the lid 8.

A tapering portion 23 is located at the end of the cylindrical portion 15 which is facing away from the lid, said tapering portion tapering in the direction of the nebulising device 3 and opening out into a fluid chamber 24. In the shown embodiment, the tapered portion 23 is composed in cross-section of a wall 26 extending substantially parallel to the progression of the later described membrane 37 as well as a wall 25 extending at an angle of between 40 and 50° to the vertical and/or to the membrane 37, and has a substantially conical form. The peak of the cone is thereby substantially in the fluid chamber 24.

Figure 1:
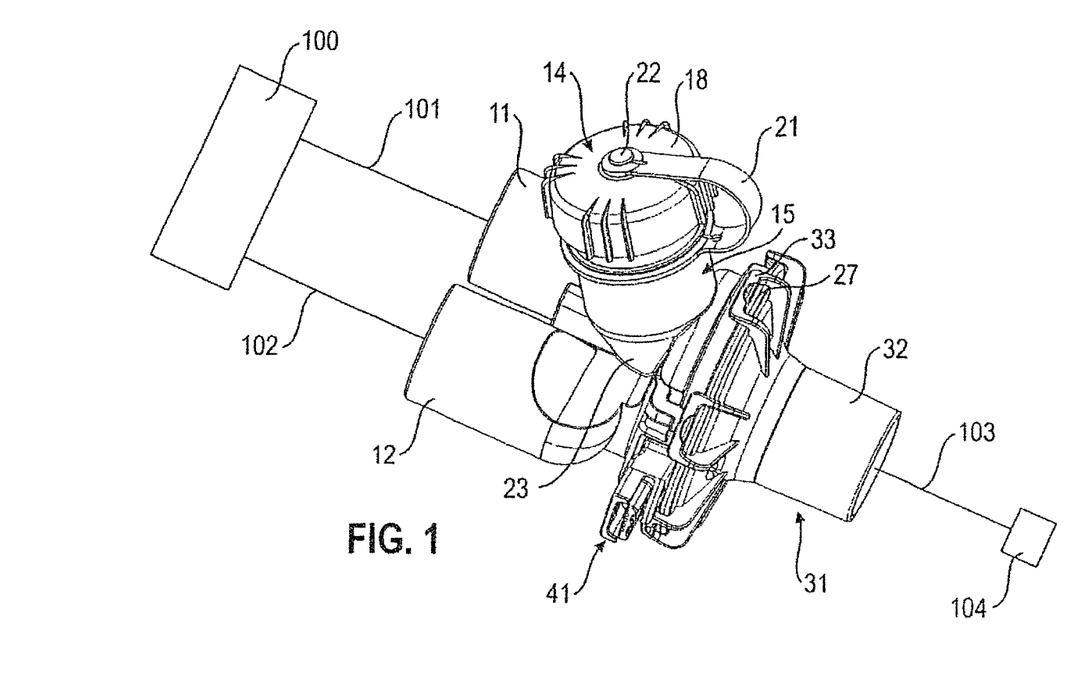
Figure 2:
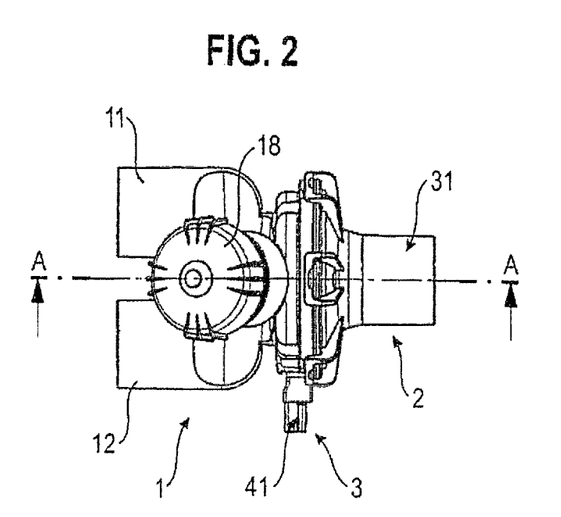
Figure 3:
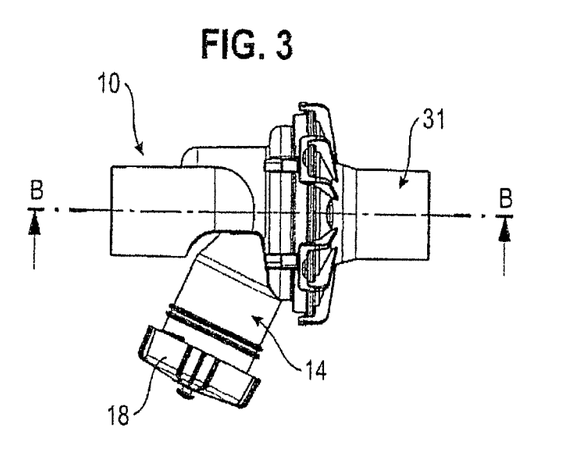

A fluid container 14 filled with fluid F is visible, for example, in FIG. 1.

The first body part 1 furthermore comprises a surrounding collar 27 at its opposite end to the first connection 10, which collar 27 can be coupled to the second body part 2 (see below). A sealing material 28 is injection moulded radially inside this collar 27 or is produced in a two-component process together with the first body part 1 that is made of a hard resilient plastic. This sealing material 28 comprises a circumferential projection 29. Also provided is a surrounding sealing lip 30 that abuts the fluid chamber 24 and is pressed against the membrane 37 for sealing such that the fluid chamber 24 is tightly sealed by the membrane 37 and the sealing lip 30.

The second body part 2 comprises the second connection 31, which is formed by a connecting piece 32. This connecting piece 32 is preferably designed in a similar manner to the tube to be respectively connected to the connecting pieces 11 and 12, which forms lines 101 and 102. By means hereof, it can be ensured that the shown nebuliser can only be integrated into the ventilation device in the proper manner. Other designs for achieving this are also conceivable. It is only important that the connections 31 and 10 are not designed in an identical manner in order to rule out the possibility that one of lines 101, 102, each formed by tubes, is connected to the connecting piece 32 or that the second line 103 that leads to the patient 104 is connected to one of the connecting pieces 11 or 12.

The second body part 2 further comprises a plurality of locking means distributed over its circumference, in this case locking catches 33. In the shown embodiment, six such locking catches 33 or snap-in hooks are provided. However, fewer or more such devices are also conceivable. The locking catches 33 are thereby designed in such a manner that in the assembled state, they can be engaged with the surrounding collar 27 of the first body part 1 in that they grip behind the collar 27 so that the first and second body parts 1 and 2 can be connected with one another. Radially inside the locking means 33, the second body part 2 furthermore comprises two surrounding, concentrically arranged webs 34 and 35 which are adapted in terms of their distance in the radial direction to the width of the projection 29 of the sealing material 28 in the radial direction such that upon engagement of the first and second body parts 1 and 2, a labyrinth seal is formed between the projection 29 and the two webs 34 and 35.

The second body part 2 furthermore comprises at least two, preferably four and possibly more supporting projections 36 for holding the aerosol generator 3 (nebulising device) (see below). These are uniformly arranged over the circumference of the second locking body 2 in pairs diametrically opposite one another and in the case of four elements, each at 90° intervals.

The second body may be designed so as to be rotationally symmetrical such that it can be connected to the first body part 1 at any orientation about its central axis.

The nebulising device 3 comprises a membrane 37 having a plurality of minute openings or holes in the micro range, which completely penetrate the membrane. The membrane 37 is preferably vibratable by means of a piezoelectric member, i.e. it can be caused to oscillate. Owing to the oscillation of the membrane, liquid on one side of the membrane, i.e. from the fluid chamber 24, will pass through the openings (not shown) and, on the other side of the membrane 37, is nebulised into a nebulisation chamber 38 formed in the body. This general principle is explained in more detail for example in U.S. Pat. No. 5,518,179, and thus a detailed description of this mode of operation will not be provided here.

Figure 5:
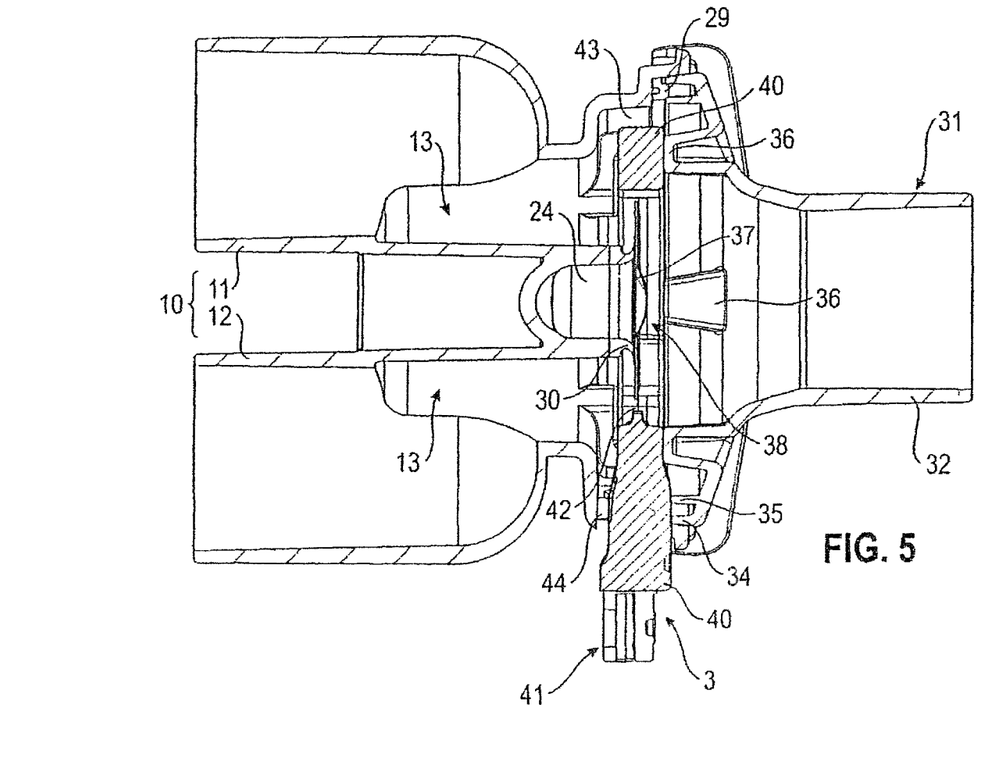

According to the invention, the membrane 37, which is a flat and even element, is held in a frame (not shown) by means of spokes (not shown in the drawings). The membrane 37 and the frame are designed so as to be substantially circular or annular. According to the preferred embodiment, the frame is insert-moulded with a soft resilient material 40, which is the same as or similar to the sealing material 38 and which surrounds the frame as well as parts of its connection 41, shown in FIG. 5, for control and power supply of the nebulising device 3. Except for the spokes along the entire circumference of the membrane, a clearance 42 is formed between the membrane 37 and the radially inner circumferential surface of the frame surrounding the membrane 37, which consists of the frame and the insert mould 40, said clearance forming part of a flow-around portion in the flow channel of the body 1, 2 that is explained later.

Furthermore, with the exception of the region of the connection 41, a further clearance 43 is formed in the assembled state between the outer surface of the frame, which consists of the insert mould 40 and the frame, and the inner circumferential surface of the body (here the first body part), said clearance 43 forming a further part of the mentioned flow-around portion. For assembly, the nebulising device 3, which is pre-assembled, is aligned with the connection 41 according to a recess and is inserted into the first body part 1, whereby the surrounding sealing lip 30 surrounds the part of the membrane 37 which is provided with openings. The second body part 2 is then attached, whereby the projections 36 press against the frame insert-moulded with the resilient material 40 and urge it in the direction of the first body part 1. The nebulising device 3 is thereby pushed in the direction of the sealing lip 30 and the membrane is thus pushed against this surrounding sealing lip 30 such that a seal is formed against the membrane or the area surrounding the membrane and the fluid chamber 24 is tightly sealed. The nebuliser is supplied ready-assembled and can also not be opened or taken apart.

Furthermore, the concentric webs 34 and 35 engage with projection 29 of the sealing material 28 and form the labyrinth seal, with the pressure of the seals against the corresponding components being maintained owing to the locking of the locking catches 33 by gripping behind the collar 27. In the region of connection 41, where part of the nebulising device exits the body 1, 2, a seal occurs between the soft resilient plastic 40 and the webs of the second locking part 2 and a projection 44 surrounding a recess in the first locking part 1 for receiving the connection 41, such that a sufficient seal is also provided here.

Figure 6:
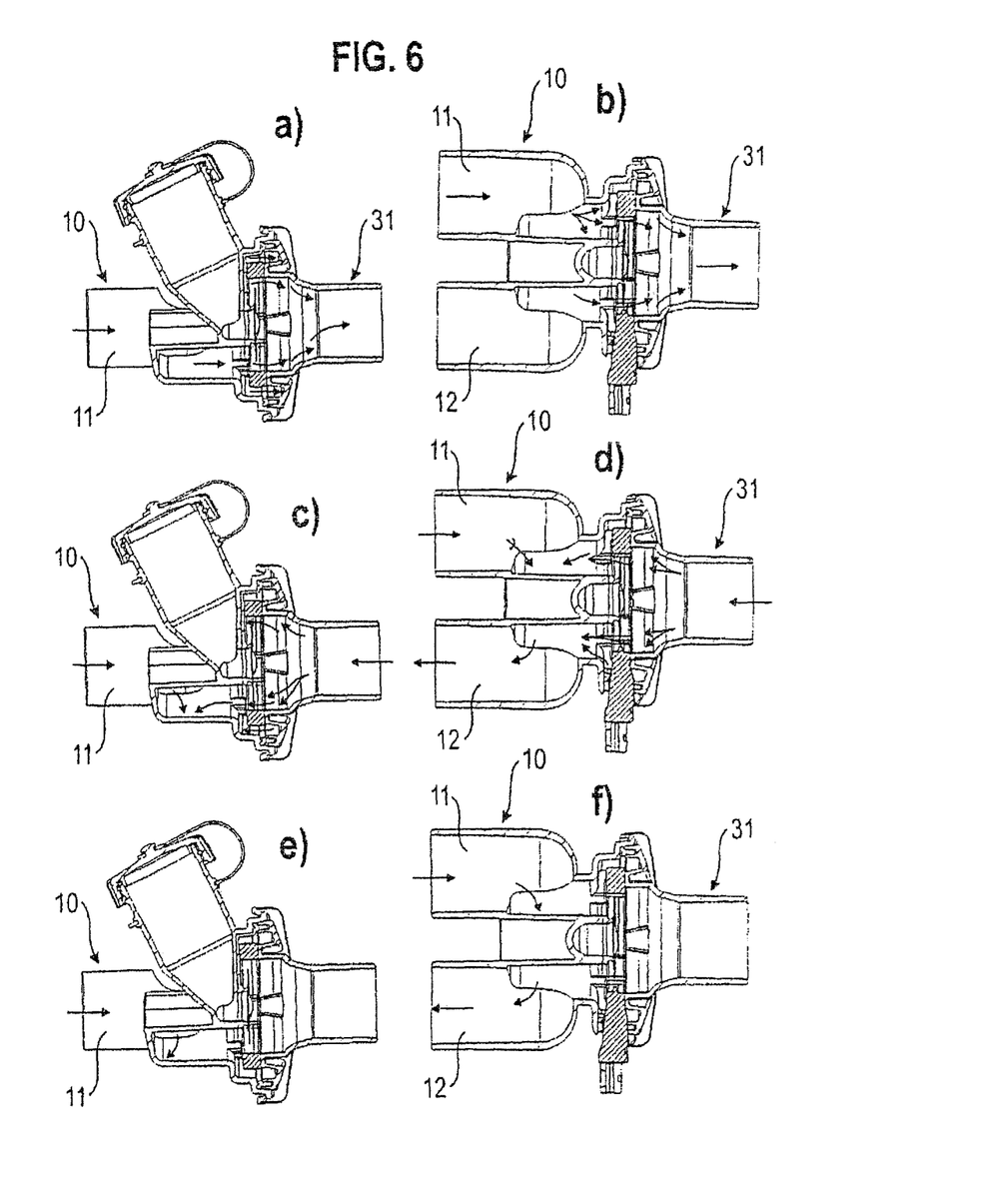

In the assembled state, the body 1, 2 forms a flow channel from connection 10 via connecting piece 11 to the second connection 31 which consists of connecting piece 32, whereby air flows around the nebulising device 3 along flow-around channels 42, 43. The direction of flow or the airflow during the inhalation phase is shown by means of arrows in FIGS. 6a and b, and the direction of flow or the airflow during the exhalation phase is shown by means of arrows in FIGS. 6c and d. It is thereby apparent that the direction of flow into the connecting piece 11 and out of the connecting piece 32 is the same and that the membrane 37 and/or the plane in which the membrane 37 lies is arranged perpendicular to this direction of flow or to the central axis of the respective connecting piece 11, 12 or 31. In the shown embodiment, this results in a fluid contained in the fluid container 14 being nebulised through the openings of the membrane into the nebulisation chamber 38 in the direction of flow, i.e. parallel thereto. The deposition of fluid on the surfaces of the flow channel or in the subsequent tubes is consequently reduced and the efficiency of the system is increased.

This design furthermore allows a bias flow to flow from the air supply line 101 into the air exhaust line 102 via the bypass 13 without passing the nebulising device 3 and in particular the nebulisation chamber 38, and thus this bias flow does not flush any aerosol (nebulised fluid) generated by the nebulising device 3 into the air exhaust line 102 outside of an inhalation cycle and/or exhalation cycle, as a result of which the efficiency of the system is further increased (see FIGS. 6e and f).

Figure 4:
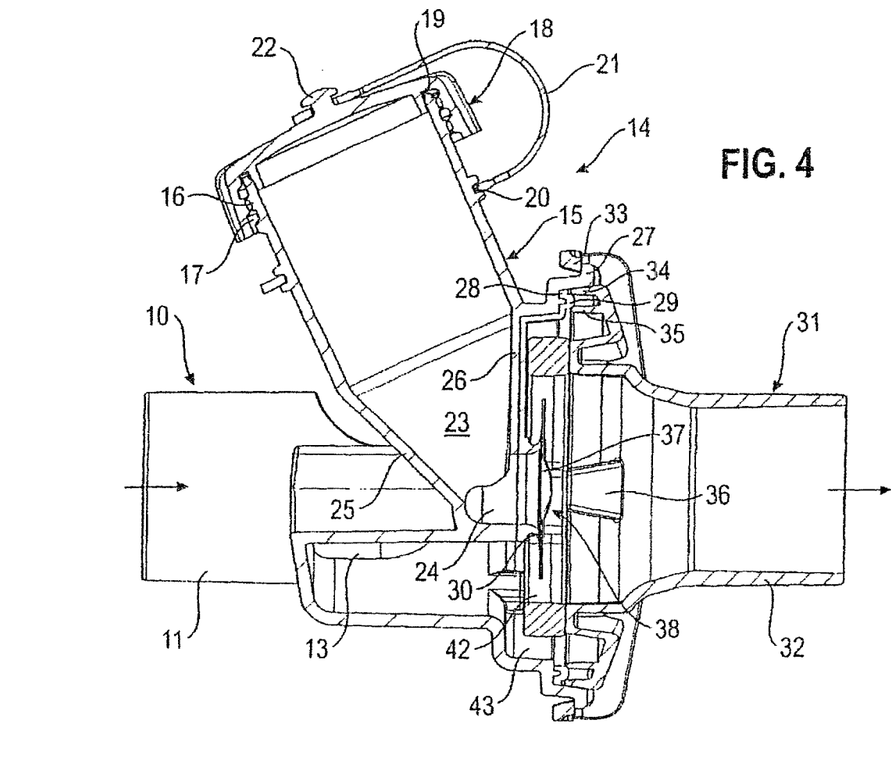

A unit that is stable against tilting is furthermore formed by the three connecting pieces 11, 12 and 32 and the integral connection of the fluid container 14 to the body 1, 2, said tilt-stable unit being of benefit for the flow behaviour of the preferably liquid fluid out of the fluid container 14 into the fluid chamber 24 and up to the membrane 37. A uniform and consistent supply of the fluid is furthermore facilitated by the design of the tapered portion 23 and in particular the incline of the wall 25, and thus even if the nebuliser shown in FIG. 4 is rotated about the central axis of the connecting piece 32 by 45° in one of the two directions, the presence of the liquid on the membrane 37 can still be reliably ensured.

The cross-sectional area of the flow-around channel 42 and 43 is thereby designed such that it is not significantly smaller than and is not significantly larger (the latter so as not to create an unnecessarily large dead volume that must be displaced during exhalation by the patient in the case of assisted respiration) than the smallest cross-sectional area in the lines of the ventilation device that lead to the patient 104 (lines 101 and 103). The lines leading to the patient 103 can be composed of a so-called catheter mount (double swivel connector) and an endotracheal tube. This prevents an increased flow resistance as well as an increased dead volume, which can both have a negative effect on the functionality of the ventilation device.

Furthermore, a tightness is achieved owing to the sealing material 28 and the insert mould 40 of the frame 39, which can also withstand a pressure of up to 100 mbar. Owing to the use of the membrane with the minute openings, a pressure loss in the system when the fluid container 14 is open is also ruled out. A flow out of the flow channel and into the fluid container 14 is not possible through the minute openings.

The nebulising device 3 can furthermore be coupled to the control of the ventilation device 100 via the connection 41 so as to trigger the nebulising device 3 only in the inhalation cycle. That is to say only when the patient 104 inhales, be it assisted or forced by the ventilation device 100, is the membrane vibrated so that nebulisation of the fluid F in the fluid container 14 occurs. The efficiency can thereby be increased even further.

Figure 7:
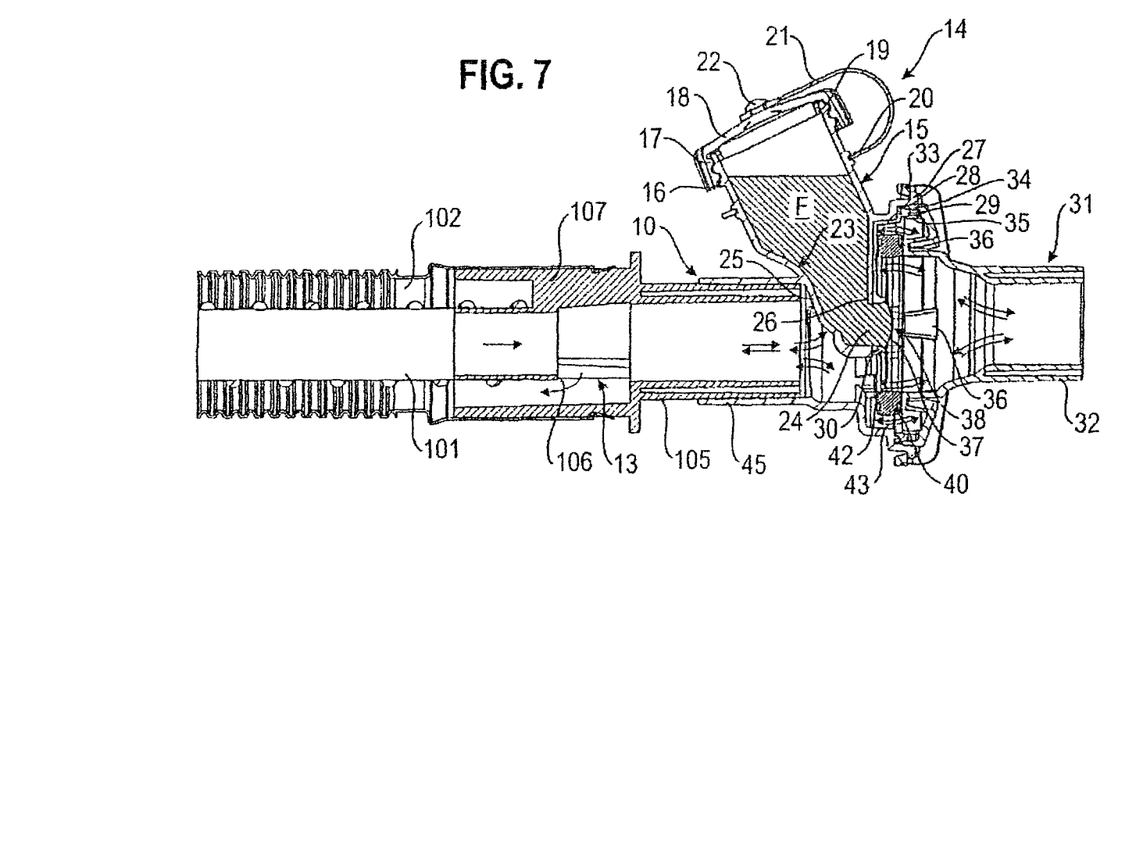

As was explained with reference to the first embodiment, the air supply line 101 and the air exhaust line 102 in the shown nebuliser are each formed by a separate tube, with the tubes being coupled to the connecting pieces 11 and 12, respectively. In the second and alternative embodiment as shown in FIG. 7, the first connection 10 comprises only one connecting piece 45, into which a corresponding connecting piece 105 of a first line 101, 102 of the ventilation device 100 can be inserted. It is also apparent from FIG. 7 that the second connection 31 comprises a connecting piece 32 having dimensions which are substantially identical to the connecting piece 105 so that the nebuliser of the present invention can be coupled into existing tube systems without any problems and can also only be assembled with the intended orientation. The lines 101 (air supply/air exhaust), 102 (air exhaust/air supply) are hereby formed in a common tube in the form of a coaxial tube, with the air supply line 101 being formed by a tube having a smaller diameter that is arranged in a tube 102 having a larger diameter and is held concentrically by means of a holder 107. The air exhaust line is formed by the clearance between the inner tube and the outer wall of the outer tube 101. The design can, however, also be reversed, as indicated above. The front face 106 of the inner tube 101 that is directed towards the nebuliser ends at a distance ahead of the membrane 37 and the nebulisation chamber 38 such that the bypass 13 (shown by means of arrows in FIG. 7) is formed in the clearance between the front face 106 and the nebulising device 3.

The embodiment according to FIG. 7 does not otherwise significantly differ from the embodiment in FIGS. 1 to 6, and thus no further explanation will be provided and reference is merely made to the embodiment as described above.

Figure 8:
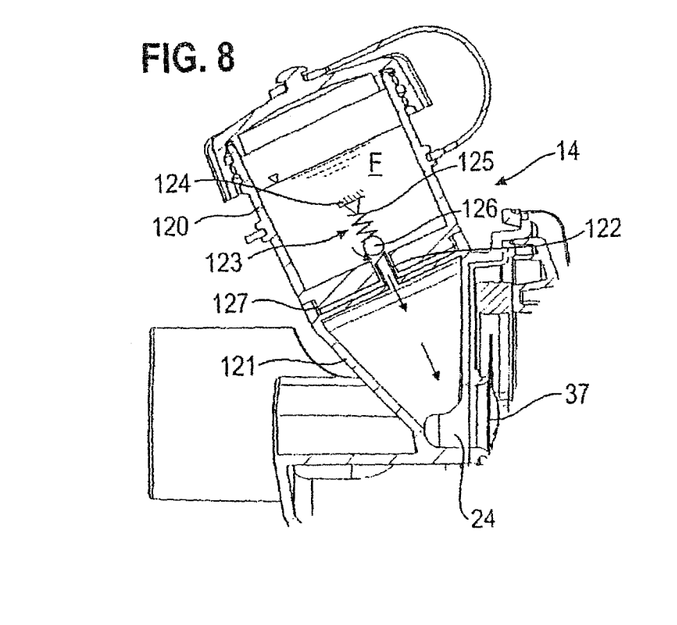
Figure 9:
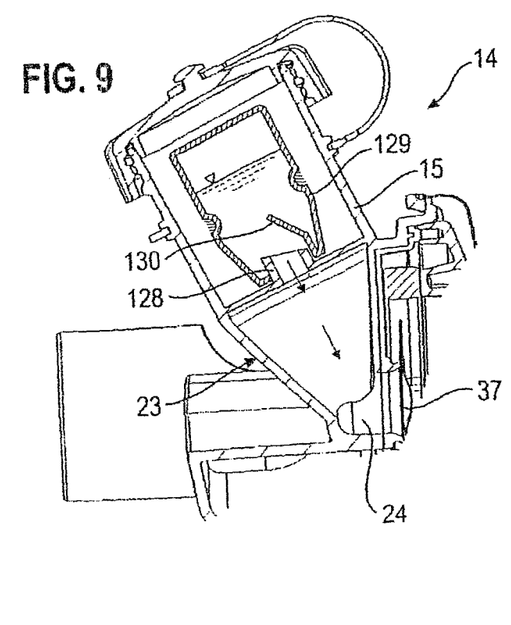

It is obvious that the present invention is not limited to the described embodiments but that various modifications may be carried out. For example, instead of the coaxial tube of FIG. 7, a tube may also be provided with a partition so as to form the two lines 101, 102. A third variant is a system consisting of two tubes (air supply and air exhaust) that are inseparably connected to a Y-piece. The installation situation of the aerosol generating means in this case also corresponds to FIG. 7. Instead of arranging the membrane 37 vertically, it is also conceivable to arrange it perpendicular to the direction of flow at a certain gradient that may deviate by up to 45° from the vertical. It is mainly important that the nebulising device in the form of the membrane lies in the flow path and that air passes around it. According to the invention, the fluid container is designed differently, with the fluid container not necessarily having to accommodate the fluid itself, but may rather have appropriate devices so as to accommodate a container directly containing the fluid, or the fluid container may itself be designed such that it can be coupled and uncoupled via an interface. For example, the tapered portion 121 in FIG. 8 could be sealed facing away from the membrane and provided with a hollow needle 122 which, upon coupling of the cylindrical portion 120, opens a valve 123 that may consist of a ball 126 and a device which urges the ball 126 against a valve seat, for example a spring 125 that rests upon a fixed bearing 124 in the cylindrical portion 120, which can also be referred to herein as an ampoule, at its end facing away from the valve seat, as a result of which the fluid can flow all at once or gradually into the fluid chamber 24 or the tapered part 121. The valve can thereby be automatically opened, for example directly upon placement of the cylindrical part 120 on the tapered part 121, for example by means of a screw thread 127, as soon as a substantially sealing connection between these elements has been established (see the schematic representation in FIG. 8). The provision of a spike 128 is also conceivable, via which an ampoule 129, which contains the fluid, is pierced. The latter is schematically shown in FIG. 9, whereby the spike pierces the bottom 130 of the ampoule 129 and folds it back so that fluid can flow into the fluid chamber 24. The spike is configured hollow for this purpose.

Furthermore, the use of a different nebulising device to the one shown is, in principle, also conceivable, for example nozzle nebulisers could also be used provided that the direction of nebulisation is substantially in, i.e. parallel to, the direction of flow between connections 10 and 31. It is furthermore also conceivable to arrange the nebuliser in the line 101 and to design the connection of lines 101, 102 and 103 via a Y-piece. However, efficiency is then reduced since the bias flow would always transport aerosol into the air exhaust line 102 unless a triggering of the nebulising device 3 in accordance with the inhalation cycle is provided so that during the bias flow, nebulisation does not occur without inhalation. It would also be conceivable, in principle, to arrange the nebuliser after a Y-piece, i.e. the nebuliser such as shown in FIG. 7 could be directly connected to a Y-piece, i.e. between the y-piece and the line 103 (catheter mount and endotracheal tube) as well as the lines 101, 102 that are coupled to the Y-piece. However, in particular the integration of the Y-piece and nebuliser, as is described in the first embodiment, is particularly preferred.

Finally, the following active ingredient classes or substances can be nebulised by the nebuliser of the present invention, however this list is not exhaustive:

The active compounds include, for example, substances selected from the group consisting of anti-inflammatory compounds, glucocorticoids, anti-allergy medicaments, antioxidants, vitamins, leukotriene antagonists, anti-infective agents, antibiotics, antifungicides, antiviral agents, mucolytic agents, decongestants, antiseptics, cytostatic agents, immunomodulators, vaccines, wound-healing agents, local anaesthetics, oligonucleotides, peptides, proteins and plant extracts.

Examples of possibly useful anti-inflammatory compounds are glucocorticoids and non-steroidal anti-inflammatory agents, such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluorcortin butyl, hydrocortisone, hydroxycortisone-17-butyrate, prednicarbate, 6-methylprednisolone aceponate, mometasone furoate, dehydroepiandrosterone sulphate (DHEAS), elastane, prostaglandin, leukotrine, bradykinin antagonists, non-steroidal anti-inflammatory drugs (NSAIDs), such as ibuprofen, including all pharmaceutically acceptable salts, esters, isomers, stereoisomers, diastereomers, epimers, solvates or other hydrates thereof, prodrugs, derivatives or any other chemical or physical forms of effective compounds, which comprise the corresponding effective residues.

Examples of anti-infective agents, the class or therapeutic category of which is understood herein as including compounds that are effective against bacterial, fungal and viral infections, i.e. including the classes of microbicides, antibiotics, fungicides, antiseptics and anti-viral agents, are

- penicillins, including benzylpenicillins (penicillin G sodium, clemizone penicillin, benzathine penicillin G), phenoxypenicillins (penicillin V, propicillin), aminobenzylpenicillins (ampicillin, amoxicillin, bacampicillin), acylaminopenicillins (azlocillin, mezlocillin, piperacillin, apalcillin), carboxypenicillins (carbenicillin, ticarcillin, temocillin), isoxazolylpenicillins (oxacillin, cloxacillin, dicloxacillin, flucloxacillin), and amiidine penicillins (mecillinam);
- cephalosporins, including cefazolins (cefazolin, cefazedone); cefuroximes (cerufoxime, cefamdole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil) and cefiximes (cefixime, cefpodoxime proxetil, cefuroxime axetil, cefetamet pivoxil, cefotiam hexetil), loracarbef, cefepime, clavulanic acid/amoxicillin, ceftobiprole;
- synergists, including beta-lactamase inhibitors, such as clavulanic acid, sulbactam and tazobactam;
- carbapenems, including imipenem, cilastin, meropenem, doripenem, tebipenem, ertapenem, ritipenam and biapenem;
- monobactams, including aztreonam;
- aminoglycosides such as apramycin, gentamicin, amikacin, isepamicin, arbekacin, tobramycin, netilmicin, spectinomycin, streptomycin, capreomycin, neomycin, paromoycin and kanamycin;
- macrolides, including erythromycin, clarithromycin, roxithromycin, azithromycin, dithromycin, josamycin, spiramycin and telithromycin;
- gyrase inhibitors or fluroquinolones, including ciprofloxacin, gatifloxacin, norfloacin, ofloxycin, levofloxacin, perfloxacin, lomefloxacin, garenoxacin, clinafloxacin, sitafloxacin, prulifloxacin, olamufloxacin, caderofloxacin, gemifloxacin, balofloxacin, trovafloxacin and moxifloxacin;
- tetracyclines, including tetracycline, oxytetracycline, rolitetracycline, minocycline, doxycycline, tigecycline and aminocycline;
- glycopeptides, including vacomycin, teicoplanin, ristocetin, avoparcin, oritavancin, ramoplanin and peptide 4;
- polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;
- sulfonamides, including sulfadiazine, sulfamethoxazole, sulfalene, co-trimoxazole, co-trimetrol, co-trimoxazine, co-tetraxazine;
- azoles, including clotrimazole, oxiconazole, miconazole, ketoconazole, itraconazole, fluconazole, metronidazole, tinidazole, bifonazole, ravuconazole, posaconazole, voriconazole and ornidazole and other anti-fungicides including flucytosine, griseofluvine, tonoftal, naftifine, terbinafine, amorolfine, ciclopiroxolamine, echinocandin, such as micafungin, caspofungin, anidulafungin;
- nitrofurans, including nitrofurantoin and nitrofuranzone;
- polyenes, including amphotericin B, natamycin, nystatin, flucocytosine;
- other antibiotics, including tithromycin, lincomycin, clindamycin, oxazolindiones (linzezolids), ranbezolid, streptogramin A+B, pristinamycin aA+B, virginiamycin A+B, dalfopristin/quinupristin (synercid), chloramphenicol, ethambutol, pyrazinamide, terizidone, dapsone, prothionamide, fosfomycin, fucidic acid, rifampicin, isoniazid, cycloserine, terizidone, ansamycin, lysostaphin, iclaprim, mirocin B17, clerocidin, filgrastim and pentamidine;

antiviral agents, including aziclovir, ganciclovir, birivudin, valaciclovir, zidovudine, didanosine, thiacytidine, stavudine, lamivudine, zalcitabine, ribavirin, nevirapirine, delaviridine, trifluridine, ritonavir, saquinavir, indinavir, foscarnet, amantadine, podophyllotoxin, vidarabine, tromantadine and proteinase inhibitors;

antiseptics, including acridine derivatives, iodine povidone, benzoates, rivanol, chlorhexidine, quaternary ammonium compounds, cetrimides, biphenylol, chlorophene and octenidine;

plant extracts or components, such as plant extracts of camomile, hamamelis, Echinacea, calendula, thyme, papain, pelargonium, pine trees, essential oils, myrtol, pinene, limonene, cineole, thymol, menthol, camphor, tannin, alpha-hederin, bisabolol, lycopodine, vitapherole;

wound-healing compounds, including dexpanthenol, allantoin, vitamins, hyaluronic acid, alpha-antitrypsin, inorganic and organic zinc salts/compounds, bismuth salts and selenium salts;

interferons (alpha, beta, gamma), tumour necrosis factors, cytokines, interleukins;

immunomodulators, including methotrexate, azathioprine, cyclosporine, tacrolismus, sirolismus, rapamycin, mofetil, mofetil-mycophenolate;

cytostatic agents and metastasis inhibitors;

alkylating agents, such as nimustine, melphanalan, carmustine, lomustine, cyclophosphamide, ifosfamide, trofosamide, chlorambucil, busulfan, treosulfan, prednimustine, thiotepa;

anti-metabolites, for example cytarabine, fluorouracil, methotrexate, mercaptopurine, thioguanine;

alkaloids such as vinblastine, vincristine, vindesine;

antibiotics such as, for example, alcarubicin, bleomycin, dactinomycin, daunorubicin, doxorubicin, epirubicin, idarubicin, mitomycin, plicamycin;

complexes of elements of the transition groups (for example, Ti, Zr, V, Nb, Ta, Mo, W, Pt) such as carboplatin, cis-platin and metallocene compounds such as, for example, titanocene dichloride;

amsacrine, dacarbazine, estramustine, etoposide, beraprost, hydroxycarbamide, mitoxanthrone, procarbazine, temiposide;

paclitaxel, iressa, zactima, poly-ADP-ribose-polymerase (PRAP) enzyme inhibitors, banoxantrone, gemcitabine, pemetrexed, bevacizumab, ranibizumab.

Examples of potentially useful mucolytic agents are DNase, P2Y2-agonists (denufosol), medicaments that affect the penetration of chlorine and sodium, such as, for example, N-(3,5-diamino-6-chloropyrazine-2-carbonyl)-N'-{4-[4-(2,3-dihydroxypropoxy)-phenyl]butyl}guanidine-methane sulfonate (PARION 552-02) heparinoids, guaifenesin, acetylcysteine, carbocysteine, ambroxol, bromhexine, tyloxapol, lecithins, myrtol and recombinant surfactant proteins.

Examples of potentially useful vasoconstrictors and decongestants that may be useful for reducing swelling of the mucous membrane are phenylephrine, naphazoline, tramazoline, tetryzoline, oxymetazoline, fenoxazoline, xylometazoline, epinephrine, isoprenaline, hexoprenaline and ephedrine.

Examples of potentially useful local anaesthetics include benzocaine, tetracaine, procaine, lidocaine and bupivacaine.

Examples of potentially useful anti-allergy agents include the aforementioned glucocorticoids, cromolyn sodium, nedocromil, cetrizine, loratidine, montelukast, roflumilast, ziluton, omalizumab, heparinoids and other antihistamines, including azelastine, cetirizine, desloratadine, ebastine, fexofenadine, levocetirizine, loratadine.

Antisense oligonucleotides are short, synthetic strands of DNA (or analogues) which are complementary or opposite to the target sequence (DNA, RNA) and which are designed such that they stop a biological process such as transcription, translation or splicing. The inhibition of gene expression hereby caused makes oligonucleotides useful for the treatment of many illnesses, depending on their composition, and numerous compounds are currently being clinically tested, such as, for example, ALN-RSV01 for the treatment of respiratory syncytial virus, AVE-7279 for the treatment of asthma and allergies, TPI-ASM8 for the treatment of allergic asthma and 1018-ISS for the treatment of cancer.

Examples of potentially useful peptides and proteins include amino acids, such as, for example, L-arginine, L-lysine, antibodies to toxins produced by microorganisms, antimicrobial peptides such as cecropins, defensins, thionins and cathelicidins.

For each of these and other explicitly mentioned examples of medicinal substances that are potentially useful for carrying out the invention, the compound names specified herein should be understood as also including any pharmaceutically acceptable salts, solvates or other hydrates, prodrugs, isomers or any other chemical or physical forms of the relevant compounds which contain the corresponding active residues.

What is claimed is:

1. Nebuliser for ventilation machines, comprising:
    a body having a first connection for connecting the nebuliser to a ventilation device and a second connection for connecting the nebuliser to a line leading to a patient, said body forming a flow channel from the first connection to the second connection; and
    a nebulising device for nebulising a fluid and introducing the nebulized fluid into the flow channel between the first connection and the second connection, wherein the nebulising device comprises a vibratable membrane that is provided with a plurality of openings for nebulising the fluid;
    a fluid container for receiving the fluid to be nebulised, which is connected to the body; and
    a nebulisation chamber, into which the fluid is to be nebulised, wherein
    the nebulisation chamber and the second connection are disposed on a first side of the membrane and the first connection is disposed on a second side of the membrane opposite to the first side with the membrane being disposed in the flow channel,
    the fluid container is connected to the body in such a manner that it can be coupled and uncoupled with the nebulising device remaining at the body or is configured to receive a fluid-containing ampoule that comes into fluid communication with the fluid container via a fluid communication interface.

2. Nebuliser according to claim 1, wherein the nebulising device is configured such that the fluid can be nebulised substantially parallel to a direction of flow from the first connection to the second connection.

3. Nebuliser according to claim 1, wherein the is arranged between said fluid container and said nebulisation chamber.

4. Nebuliser according to claim 1, wherein the nebulisation chamber is disposed between the membrane and the second connection.

5. Nebuliser according to claim 1, wherein the fluid container comprises a tapering in the direction of the membrane, which opens out into a fluid chamber closed by said membrane.

6. Nebuliser according to claim 5, wherein at least a partial section of the tapering that is facing away from the membrane extends with an angle range of between 10° and 40° to the vertical.

7. Nebuliser according to claim 1, wherein the flow channel comprises a flow-around portion, which is configured in a radial direction between the membrane and the body, and which has a cross-sectional area that corresponds approximately to a smallest cross-sectional area of a line of the ventilation device that leads to the patient.

8. Nebuliser according to claim 7, wherein the membrane is hung in a frame surrounding said membrane by means of spokes such that at least a part of the flow-around portion is formed between the frame and the membrane.

9. Nebuliser according to claim 1, wherein the membrane is arranged substantially perpendicular to a direction of flow from the first connection to the second connection.

10. Nebuliser according to claim 1, wherein the fluid communication interface is formed by an opening device and configured to receive the fluid containing ampoule to be opened by means of the opening device.

11. Nebuliser according to claim 10, wherein the opening device is a hollow spike.

12. Nebuliser according to claim 1, wherein the fluid communication interface is formed by a hollow needle and a valve which is opened upon receipt of the fluid containing ampoule by means of the hollow needle.

13. Ventilation machine comprising a ventilation device having an air supply line for providing respiratory air, an air exhaust line for returning consumed air, and a second line leading to a patient, as well as a nebuliser according to claim 1, wherein the first connection of the body is connected at least to the air supply line.

14. Ventilation machine according to claim 13, wherein the first connection of the body is further connected to the air exhaust line and the second connection of the body is connected to the second line.

15. Ventilation machine according to claim 13, further comprising a control via which the nebulising device can be triggered in correspondence with the inhalation cycle so that nebulisation of the fluid can only be triggered during the inhalation cycle.

16. Nebuliser according to claim 1, wherein the nebulising device is configured such that the fluid can be nebulised in a direction of flow from the first connection to the second connection.

* * * * *

UNITED STATES PATENT AND TRADEMARK OFFICE
CERTIFICATE OF CORRECTION

Page 1 of 1

PATENT NO.         : 9,095,676 B2
APPLICATION NO.    : 13/783642
DATED              : August 4, 2015
INVENTOR(S)        : Thomas Gallem et al.

It is certified that error appears in the above-identified patent and that said Letters Patent is hereby corrected as shown below:

In The Claims

At column 14, claim 3, line 63 should read as follows:

3. Nebuliser according to claim 1, wherein the membrane is arranged

Signed and Sealed this
Fifteenth Day of December, 2015

Michelle K. Lee
*Director of the United States Patent and Trademark Office*